United States Patent [19]
Chen

[11] 3,972,328
[45] Aug. 3, 1976

[54] SURGICAL BANDAGE
[75] Inventor: James Ling Chen, East Brunswick, N.J.
[73] Assignee: E. R. Squibb & Sons, Inc., Princeton, N.J.
[22] Filed: July 28, 1975
[21] Appl. No.: 599,804

[52] U.S. Cl. ............................................. 128/156
[51] Int. Cl.[2] ........................................ A61L 15/00
[58] Field of Search ........................ 128/155–157, 128/165, 169, 296, 166; 428/354, 355

[56] References Cited
UNITED STATES PATENTS

| | | | |
|---|---|---|---|
| 3,523,846 | 8/1970 | Muller | 128/156 X |
| 3,536,072 | 10/1970 | Quello | 128/169 |
| 3,648,692 | 3/1972 | Wheeler | 128/156 |
| 3,649,436 | 3/1972 | Buese | 128/156 X |
| 3,805,781 | 4/1974 | Hoey | 128/166 |
| 3,908,645 | 9/1075 | Sandvig | 128/156 X |

Primary Examiner—Lawrence W. Trapp
Attorney, Agent, or Firm—Lawrence S. Levinson; Merle J. Smith; Stephen B. Davis

[57] ABSTRACT

Bandage which can be applied to the skin in place of the normal surgical dressings comprising an adhesive layer, a layer of flexible semi-open cell polymeric foam, and an outer water impervious flexible polymeric film coating.

17 Claims, 2 Drawing Figures

SURGICAL BANDAGE

BACKGROUND OF THE INVENTION

Chen in U.S. Pat. No. 3,339,546 discloses a bandage to be applied to a body surface comprising a water impervious film having an adhesive gum-like bonding composition secured to one side. The bonding composition is a blend of a water soluble or water swellable hydrocolloid admixed with a water insoluble viscous gum-like elastic binder.

Crowe in U.S. Pat. Nos. 3,122,140, 3,122,141, 3,122,142 and 3,156,242 disclose medical dressings comprising a sheet of foam material such as polyurethane with fiber webs acting as capillaries dispersed throughout. Buese in U.S. Pat. No. 3,649,436, Lindquist et al. in U.S. Pat. No. 3,665,918 and Wharton et al. in British Pat. No. 1,253,845 disclose medical dressings comprising a sheet of compressed open cell polyurethane foam coated on one side with a pressure sensitive adhesive. In addition, Lindquist et al. disclose that the other side of the compressed foam may have a porous plastic coating. Bandages in which an open cell polyurethane foam is applied directly to the wound are disclosed in U.S. Pat. Nos. 3,113,568 to Robins, 3,157,178 to Bentov, 3,491,753 to Milton et al., and 3,648,692 to Wheeler. Other prior art medical devices containing a layer of open cell foam include a traction strip in U.S. Pat. No. 3,536,072 to Quello, a surgical drape in U.S. Pat. No. 3,669,106 to Schrading et al., and a surgical pad in U.S. Pat. No. 3,301,254 to Schiekendanz.

SUMMARY OF THE INVENTION

This invention is directed to an improved medical dressing consisting of three components. The middle layer is a semi-open cell polymeric flexible foam having attached to one side a water impervious flexible polymeric film and attached to the other side a pressure sensitive adhesive composition.

DETAILED DESCRIPTION

Figure 1:
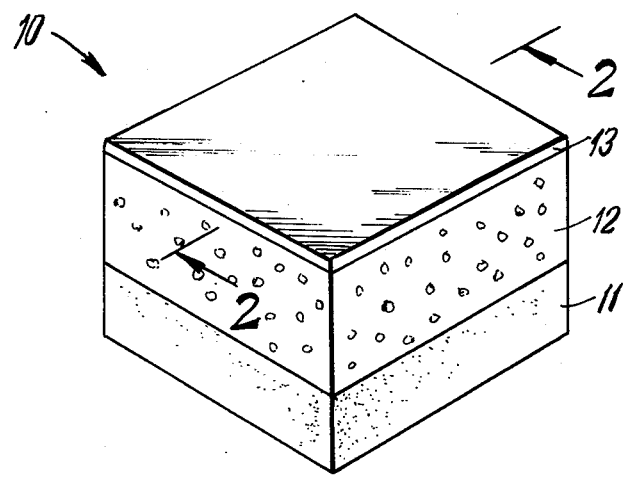
FIG. 1 is an overall view of the bandage (greatly enlarged).
Figure 2:
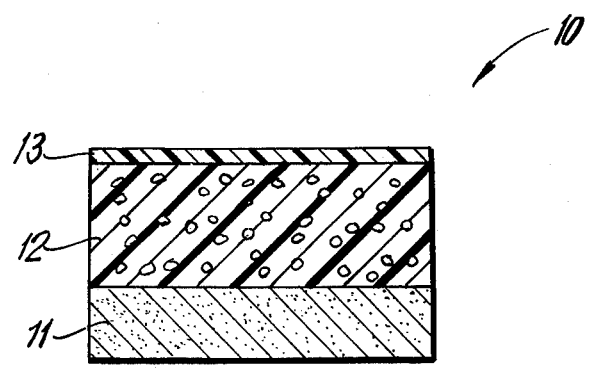
FIG. 2 is a front view along the line 2—2 of FIG. 1.

Referring now to the drawings in more particular detail, the bandage 10 comprises pressure sensitive adhesive composition layer 11, a semi-open cell polymeric foam layer 12, and outer polymeric film coating 13.

The pressure sensitive adhesive composition layer 11 comprises a pressure sensitive rubbery elastomer adhesive material having intimately dispersed therein a water soluble or swellable hydrocolloid or mixture of hydrocolloids, a tackifier, and a plasticizer or solvent. Suitable rubbery elastomers include natural or synthetic viscous gum-like substances such as natural rubber, silicone rubber, acrylonitrile rubber, polyurethane rubber, polyisobutylene, etc., with a mixture of polyisobutylenes of a molecular weight of 10,000 to 11,700 and 81,000 to 99,000 being preferred. Suitable hydrocolloids include polyvinyl alcohol, powdered pectin, gelatin, sodium carboxymethylcellulose, high molecular weight carbowax, carboxypolymethylene, etc., with a mixture of gelatin and sodium carboxymethylcellulose being preferred. Suitable plasticizers or solvents include mineral oil and petrolatum with mineral oil being preferred. Terpene resin is the preferred tackifier. The viscous gum-like substance acts as a binder for the hydrocolloid particles and, in addition, renders the final adhesive composition tacky, elastic, and pliable. It is preferable to also include an antioxidant such as butylated hydroxytoluene or butylated hydroxyanisole within the adhesive composition to prolong the shelf life of the bandage.

The hydrocolloid or mixture of hydrocolloid should comprise more than about 30% by weight of the pressure sensitive adhesive composition and preferably from about 40 to about 50% by weight of the adhesive composition. The adhesive composition can vary in thickness from about 5 to about 30 mils, preferably 5 to 15 mils.

The semi-open cell elastic or flexible foam layer 12 can be formed from various elastomer materials such as polyester or polyether polyurethane foams, styrene-butadiene foams, and possibly certain rubber-based foams, etc. The material employed should of course be non-toxic and stable. The preferred material is a flexible polyurethane foam having from about 50 to about 100 cells per linear inch with about 80 cells per linear inch being most preferred. By semi-open it is meant that the percentage of open or ruptured cells is from about 30 to about 70%. The semi-open cell foam layer can vary in thickness from about 20 to about 50 mils.

The outer polymeric elastic or flexible film coating 13 can be formed from a water impermeable pliable elastomer material such as flexible polyurethane, polyacrylate, natural rubber, etc. The material employed may be somewhat gas permeable so as to aid in the passage of air to the surface of the skin and should be transparent or sufficiently translucent so as to permit viewing of the covered portion of the skin without removal of the bandage. Preferably the material employed is flexible polyurethane. The coating 13 can be applied as a single layer or a plurality of layers so that the total thickness of the coating 13 is from about 1.0 to about 3.0 mils, preferably about 1.5 to 2.0 mils.

During packaging of the bandage a piece of silicone coated release paper (not shown in the drawings) is attached to the exposed side of the adhesive bonding composition 11.

The bandage 10 is prepared by forming a mixture of the hydrocolloid, rubbery elastomer, tackifier and plasticizer, as well as other optional ingredients such as antioxidant, in an organic solvent such as heptane or hexane. The resulting adhesive slurry is applied to a portion of silicone coated release paper and the solvent is evaporated. Upon drying the hydrocolloid is dispersed throughout the adhesive layer. This material is then compressed together with a laminate of semi-open cell flexible polymeric elastomer foam having a water-impermeable flexible polymeric elastomer film coating on one side. One process of forming such a laminate is disclosed by Sutton in U.S. Pat. No. 3,547,753. Of course, other methods may be employed to form this laminate. The resulting bandage including the silicon coated release paper can be wound into rolls or cut into individual size bandages and packaged.

The bandage of the instant invention has numerous advantages over those of the prior art. The hydrocolloid present in the adhesive layer absorbs moisture such as perspiration and wound exudate and transfers such moisture from the surface of the skin to the layer of open-cell foam where it can evaporate through the sides of the bandage. This is in contrast to bandages having a conventional pressure sensitive adhesive which does not permit the escape of moisture from the skin surface. The build-up of such moisture invariably causes skin rash and irritation and will eventually weaken the adhesive bond causing the bandage to fall off. The adhesive layer of the instant bandage by regulating the moisture level at the surface of the skin enables the bandage to remain firmly in place for long periods of time and reduces or eliminates the need for the dressing to be changed. The laminate of open-cell foam and polymeric film coating provides added flexibility to the bandage to allow complete freedom of movement and comfort and also increase the retension of the bandage on the skin especially at portions of the body such as the knee or elbow which undergo stress. The outer polymeric film coating provides a smooth surface which reduces friction between the bandage and clothing or bedding so as to prevent accidental dislodging of the bandage. The film coating also strengthens the open-cell foam layer and allows the bandage to be removed and peeled off without breaking.

Air is able to flow through the sides of the open-cell foam and permeate down through the adhesive layer to the treated portion of the skin. However, unlike the prior art bandages where the foam directly contacts the skin, the adhesive layer seals off the wounded area so as to prevent contamination and bacterial infection. The adhesive layer of this bandage unlike conventional moisture blocking pressure sensitive adhesives does not cause irritation, itch, or excoriation of the skin. This bandage can be easily removed after the wound heals.

The materials employed in the three components of the bandage enable the bandage to be sterilized by various means such as autoclaving or gamma radiation. The bandage is nearly transparent or translucent to the extent that the wound can be observed without the necessity of removing the bandage.

The instant bandage is also useful in burn therapy. As discussed above, the adhesive layer seals off the wound and prevents the danger of infection, the open-cell foam permits adequate air and water vapor transmission and gives the bandage added flexibility, and the overall bandage provides good visibility of the area being treated. The adhesive layer due to the presence of hydrocolloid is able to absorb exudate from the burn surface and transport such material to the upper layer adjoining the semi-open cell foam from which is is dissipated as a vapor by the air flowing through the sides of the foam layer. At the same time, excessive loss of fluid from the burn surface is regulated by the adhesive layer and the water-impervious outer polymeric film coating. Since the hydrocolloid within the adhesive layer becomes mucilaginous when contacted with the burn exudate, removal of the bandage is possible without damage to the surface of the injured skin and with a minimum of pain.

The following example is illustrative of the invention.

EXAMPLE 60 kg. of polyisobutylene rubber of an average molecular weight of from 81,000 to 99,000, 54 kg. of sodium carboxymethylcellulose and 45 kg. of gelatin (100 mesh) are kneaded to form a mixture in which the finely divided pieces of rubber are kept separate and prevented from sticking together by the hydrocolloids. This mixture is added to a solution of heptane containing 54 kg. of polyisobutylene of an average molecular weight of 10,000 to 11,700, 60 kg. of tackifier (terpene resin), 1.5 kg. of antioxidant (butylated hydroxytoluene), and 25.5 kg. of mineral oil to form an adhesive slurry. A portion of this slurry is poured onto a sheet of silicone coated release paper and the solvent is evaporated.

A second laminate is formed consisting of semi-open cell flexible polyurethane foam (the foam has about 80 cells per linear inch with from about 30 to about 70% of the cells ruptured) having a thickness of about 30 mils coated with flexible polyurethane of about 2 mils thickness.

The adhesive/release paper laminate and the flexible polyurethane foam/flexible polyurethane laminate are gently compressed together (the foam contacting the adhesive) by passing through pressure rollers to form the bandage.

What is claimed is:

1. A bandage comprising a pressure sensitive adhesive layer, a layer of semi-open cell flexible polymeric foam attached to said adhesive layer, and a water-impervious flexible polymeric film attached to the opposite side of said foam layer wherein said adhesive layer comprises a rubbery elastomer having dispersed therein a water soluble or swellable hydrocolloid or mixture of hydrocolloids, tackifier, and plasticizer.

2. The bandage of claim 1 wherein said hydrocolloid is selected from the group consisting of polyvinyl alcohol, powdered pectin, gelatin, sodium carboxymethylcellulose, high molecular weight carbowax, carboxypolymethylene, and mixtures thereof.

3. The bandage of claim 2 wherein said hydrocolloid or hydrocolloid mixture comprises more than about 30% by weight of the adhesive layer.

4. The bandage of claim 3 wherein said hydrocolloid or hydrocolloid mixture comprises from about 40 to about 50% by weight of the adhesive layer.

5. The bandage of claim 1 wherein said rubbery elastomer is selected from the group consisting of natural rubber, silicone rubber, acrylonitrile rubber, polyurethane rubber, and polyisobutylene.

6. The bandage of claim 1 wherein said semi-open cell flexible polymeric foam has from about 50 to about 100 cells per linear inch with from about 30 to about 70% of the cells ruptured.

7. The bandage of claim 1 wherein said adhesive layer is from about 5 to about 30 mils in thickness, said foam layer is from about 20 to about 50 mils in thickness, and said water-impervious film is from about 1.0 to about 3.0 mils in thickness.

8. The bandage of claim 1 including a layer of release paper attached to the exposed bottom of said adhesive layer.

9. A bandage comprising a pressure sensitive adhesive layer, a layer of semi-open cell flexible polymeric foam attached to said adhesive layer having from about 50 to about 100 cells per linear inch with from about 30 to about 70% of the cells ruptured, and a water-impervious flexible polymeric film attached to the opposite side of said foam layer wherein said adhesive layer comprises a rubbery elastomer having dispersed therein a water soluble or swellable hydrocolloid or mixture of hydrocolloids, a tackifier, and a plasticizer, and wherein said hydrocolloid comprises more than about 30% by weight of the adhesive layer and is selected from the group consisting of polyvinyl alcohol, powdered pectin, gelatin sodium carboxymethylcellulose, high molecular weight carbowax, carboxypolymethylene, and mixtures thereof and said elastomer is selected from the group consisting of natural rubber, silicone rubber, acrylonitrile rubber, polyurethane rubber, and polyisobutylene.

10. The bandage of claim 9 wherein said pressure sensitive adhesive layer contains from about 40 to about 50% by weight of the hydrocolloid or hydrocolloid mixture and also contains an antioxidant.

11. The bandage of claim 10 wherein said pressure sensitive adhesive layer is from about 5 to 30 mils in thickness, said foam layer is from about 20 to about 50 mils in thickness, and said water-impervious film is from about 1.0 to about 3.0 mils in thickness.

12. The bandage of claim 11 wherein said elastomer is polyisobutylene and said hydrocolloid is a mixture of sodium carboxymethylcellulose and gelatin.

13. The bandage of claim 12 wherein said flexible polymeric foam is flexible polyurethane foam and said water-impervious flexible polymeric film is flexible polyurethane.

14. The bandage of claim 13 wherein said pressure sensitive adhesive layer consists of a polyisobutylene having an average molecular weight of from 81,000 to 99,000, polyisobutylene having an average molecular weight of 10,000 to 11,700, sodium carboxymethylcellulose, gelatin, terpene resin, mineral oil, and butylated hydroxytoluene.

15. The bandage of claim 14 wherein said adhesive layer is of from about 5 to about 15 mils in thickness, said flexible polyurethane film is of from about 1.5 to about 2 mils in thickness, and said flexible polyurethane foam contains about 80 cells per linear inch.

16. The bandage of claim 15 including a layer of silicone coated release paper attached to the exposed bottom of said pressure sensitive adhesive layer.

17. The method of forming the bandage of claim 16 comprising the steps of kneading polyisobutylene rubber of an average molecular weight of 81,000 to 99,000, sodium carboxymethylcellulose, and gelatin; adding this kneaded mixture with vigorous agitation to a heptane solution containing a polyisobutylene sticky mass of an average molecular weight of from 10,000 to 11,700, terpene resin, mineral oil, and butylated hydroxytoluene to dissolve the polyisobutylenes, terpene resin, mineral oil and butylated hydroxytoluene and form an adhesive slurry containing finely divided insoluble sodium carboxymethylcellulose and gelatin; pouring said slurry onto a sheet of silicone coated release paper and drying to evaporate the heptane and form an adhesive/paper laminate; forming a second laminate consisting of semi-open cell flexible polyurethane foam having about 80 cells per linear inch with from about 30 to about 70% of the cells ruptured and a flexible polyurethane film coating; joining the two laminates with the exposed surface of the foam contacting the exposed surface of the adhesive layer by passing gently between pressure rollers.

* * * * *